United States Patent [19]
Scheuermann et al.

[11] 3,983,117
[45] Sept. 28, 1976

[54] 6-TRIAZINYLAMINOBENZOFURANS

[75] Inventors: Horst Scheuermann, Ludwigshafen; Wolfgang Mach, Hockenheim, both of Germany

[73] Assignee: BASF Aktiengesellschaft, Ludwigshafen (Rhine), Germany

[22] Filed: June 24, 1974

[21] Appl. No.: 482,252

[30] Foreign Application Priority Data
June 27, 1973 Germany.............................. 2332597

[52] U.S. Cl............................. 260/249.8; 260/249.5; 260/757 N; 260/249.6; 260/249.9; 260/247.1 M; 260/247.5 C; 252/301.25; 8/190
[51] Int. Cl.²........................................ C07D 251/52
[58] Field of Search........... 260/249.5, 249.6, 249.8, 260/249.9

[56] References Cited
UNITED STATES PATENTS
3,671,524  6/1972  Suzuki .............................. 260/249.5

*Primary Examiner*—John M. Ford
*Attorney, Agent, or Firm*—Johnston, Keil, Thompson & Shurtleff

[57] ABSTRACT

6-N-triazinylaminobenzofurans and their production. The compounds are suitable for the optical brightening of natural and synthetic fibers and also of plastics materials, particularly of polyamides, cellulose esters, polyesters and acrylonitrile polymers.

5 Claims, No Drawings

6-TRIAZINYLAMINOBENZOFURANS

The invention relates to 6-N-triazinylaminobenzofurans of the formula (I):

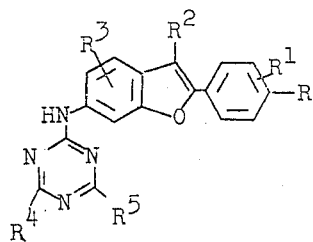

in which
R, $R^1$ and $R^3$ independently of one another may be hydrogen, chloro, bromo, cyano, carboxyl, a sulfo group, phenylsulfony, alkyl, alkoxy, carboalkoxy, alkylsulfonyl or alkoxysulfonyl of one to five carbon atoms per alkyl group, carbamoyl or sulfamoyl which may be substituted once or twice by alkyl of one to four carbon atoms, β-hydroxyalkyl of two to four carbon atoms or β-carboalkoxyalkyl of four to nine carbon atoms, and in the case of two substituents on the carbamoyl or sulfamoyl the two substituents may be combined via the amide nitrogen to form a ring;

$R^2$ is hydrogen, alkyl of one to five carbon atoms or phenyl, $R^4$ and $R^5$ independently of one another may be hydrogen, alkyl of one to four carbon atoms, alkenyl of one to four carbon atoms, cycloalkyl, aralkyl of seven to ten carbon atoms, aryl, chloro, hydroxy, alkoxy of one to eight carbon atoms, aryloxy, alkylmercapto of one to four carbon atoms, arylmercapto or a

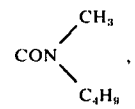

group;

$R^6$ and $R^7$ independently of one another are hydrogen or alkyl of one to eight carbon atoms, alkyl of two to eight carbon atoms substituted by hydroxy, alkoxy, acyloxy, amino or amino substituted once, twice or three times on nitrogen by cycloaliphatic radicals of six to twelve carbon atoms, araliphatic radicals of seven to ten carbon atoms or aromatic isocyclic radicals of six to ten carbon atoms, and $R^6$ and $R^7$ together with the nitrogen atom may be combined to form a saturated heterocyclic radical.

The following are examples of specific radicals for R, $R^1$ and $R^3$: methyl, ethyl, propyl, isobutyl, amyl, methoxy, ethoxy, propoxy, butoxy, isopropoxy, isobutoxy, tert.-butoxy, amyloxy, carbomethoxy, carboethoxy, carbobutoxy, carbo-β-hydroxyethyl, carbo-β-methoxyethoxy, N-methylcarbamoyl, N-ethylcarbamoyl, N-butylcarbamoyl, N,N-dimethylcarbamoyl, N,N-diethylcarbamoyl, N,N-dibutylcarbamoyl, methylsulfonyl, ethylsulfonyl, methoxysulfonyl, ethoxysulfonyl, butoxysulfonyl, methylaminosulfonyl, dimethylaminosulfonyl, butylaminosulfonyl and radicals of the formulae:

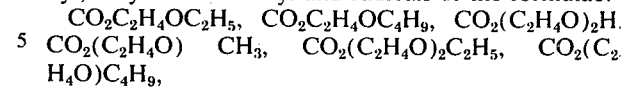

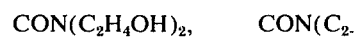

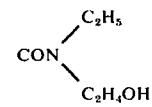

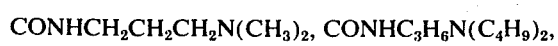

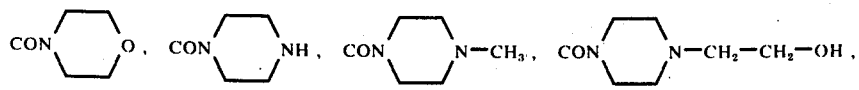

$SO_2NHCH_2CH_2$—OH, $SO_2N(CH_2CH_2OH)_2$, $SO_2N(CH_2CH_2OCOCH_3)_2$,

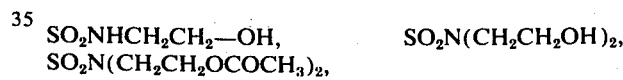

$SO_2NHC_3H_6N(CH_3)_2$, $SO_2NHC_3H_6N(C_4H_9)_2$,

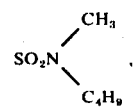

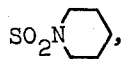, 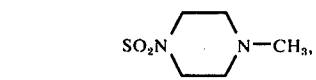

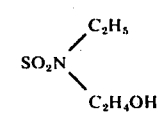

$SO_2OC_2H_4OCH_3$, $SO_2OC_2H_4OC_2H_5$, $SO_2OC_2H_4OC_4H_9$, $SO_2(OC_2H_4)_2OCH_3$, $SO_2(OC_2H_4)_2OC_2H_5$ and $SO_2(OC_2H_4)OC_4H_9$.

Examples of individual radicals for $R^4$ and $R^5$ are: methyl, ethyl, propyl, isobutyl, propenyl, butenyl, cyclohexyl, methylcyclohexyl, benzyl, β-phenylethyl, phenyl, tolyl, methoxyphenyl, naphthyl, methoxy, ethoxy, propoxy, butoxy, amyloxy, phenoxy, methylmercapto, ethylmercapto, n-butylmercapto and phenylmercapto.

Examples of radicals for $R^6$ and $R^7$ are: methyl, ethyl, isopropyl, butyl, hexyl, β-ethylhexyl, β-hydroxyethyl, β-hydroxypropyl, γ-hydroxypropyl, β-methoxyethyl, β-ethoxyethyl, γ-methoxypropyl, γ-ethoxypropyl, γ-hexoxypropyl, γ-propionylpropyl, γ-benzoyloxypropyl, γ-dimethylaminopropyl, γ-dibutylaminopropyl, γ-trimethylammoniumpropyl, γ-methyldibutylammoniumpropyl, γ-ethyldibutylammoniumpropyl, γ-ethyldimethylammoniumpropyl, β-aminoethyl, ω-aminohexyl, cyclohexyl, benzyl, phenylethyl, phenyl, totyl, dimethylphenyl and naphthyl.

When $R^6$ and $R^7$ together with the nitrogen atom form a heterocyclic radical this may be for example the radical of pyrrolidine, piperidine, morpholine, piperazine, N-methylpiperazine or N,N-dimethylpiperazinium.

In the compounds with one or more quaternary nitrogen atoms falling under the 6-N-triazinylaminobenzofuran compounds of formula (I) according to the invention the equalization of the charge is effected by one or more anions such as are conventionally used for other, known, quaternary nitrogen atoms, for example $CH_3SO_4^{(-)}$, $C_2H_5SO_4^{(-)}$, $Cl^{(-)}$, $Br^{(-)}$, $NO_3^{(-)}$, $SO_4^{(-)}$, $CH_3COO^{(-)}$, $HCOO^{(-)}$, $BF_4^{(-)}$.

Particular industrial importance attaches to compounds of the formula (I) in which $R^2$ and $R^3$ are hydrogen or methyl, R and $R^1$ are hydrogen, methyl, methoxy, chloro, cyano, carbomethoxy, carboethoxy, carbobutoxy, carbo-β-ethoxyethoxy, N-methylcarbamoyl, N-butylcarbamoyl, N,N-dimethylcarbamoyl, N,N-diethylcarbamoyl, N,N-dibutylcarbamoyl and the radicals of the formulae:

$CO_2C_2H_4OC_4H_9$, $CON(C_2H_4OH)_2$,

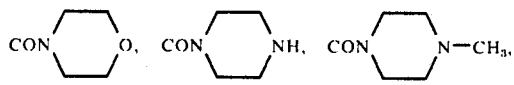

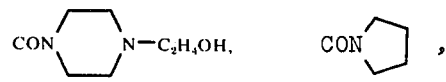

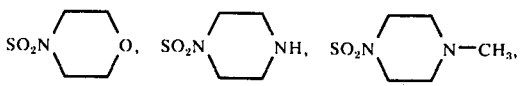

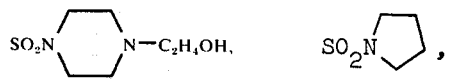

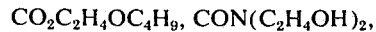

$SO_2N(CH_2-CH_2-OH)_2$, and $R^4$ and $R^5$ independently of one another may be chloro, methoxy, ethoxy, isopropoxy, isobutoxy, n-butoxy, phenoxy, butylmercapto, amino, methylamino, ethylamino, isopropylamino, n-butylamino, dimethylamino, diethylamino, dibutylamino, methylbutylamino, β-hydroxyethylamino, β-methoxyethylamino, γ-hydroxpropylamino, γ-ethoxypropylamino, γ-trimethylammoniumpropylamino, γ-methyldibutylammoniumpropylamino, γ-ethyldibutylammoniumpropylamino, γ-ethyldimethylammoniumpropylamino, β-aminoethylamino, cyclohexylamino, benzylamino or phenylethylamino.

Compounds having very good properties are those in whose two radicals $R^4$ and $R^5$ one is or both are pyrrolidine, morpholine, N-methylpiperazine or N,N-dimethylpiperazinium.

Specifically the following compounds are of particular value industrially:

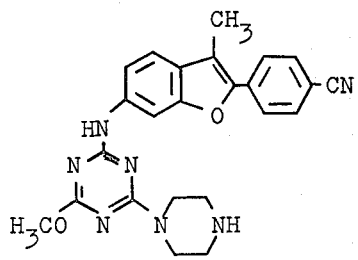

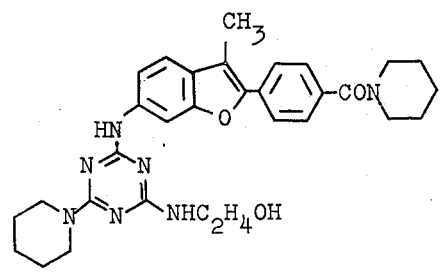

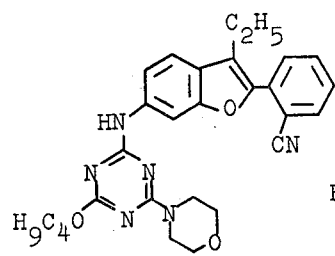

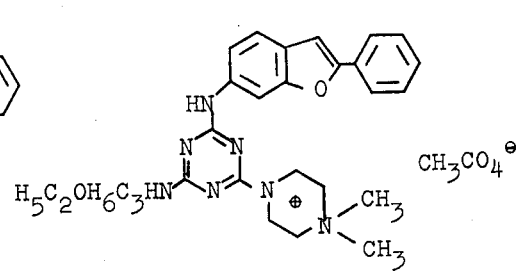

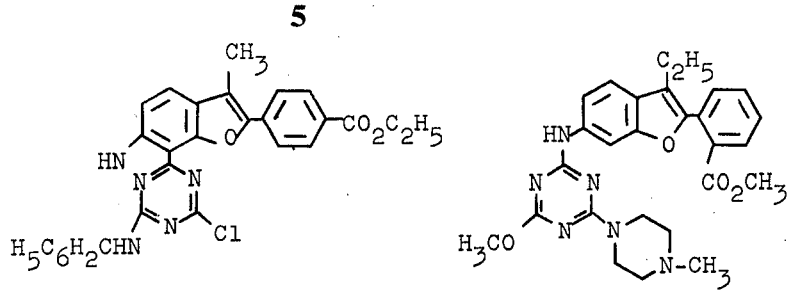
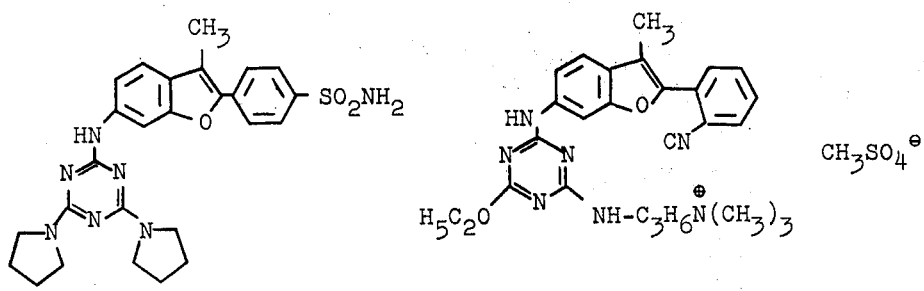
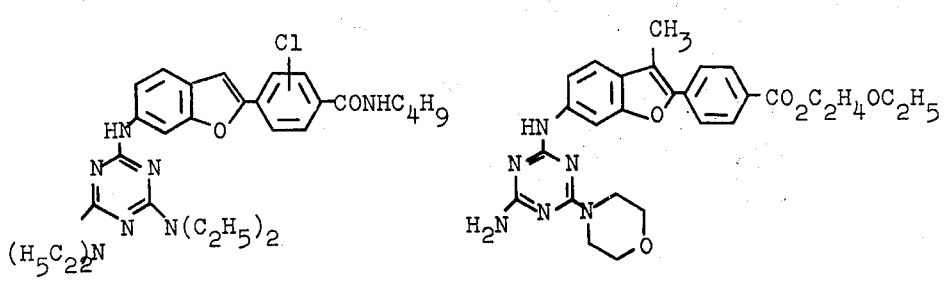
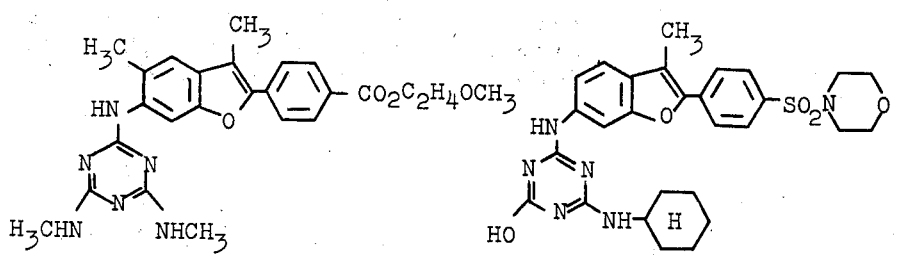
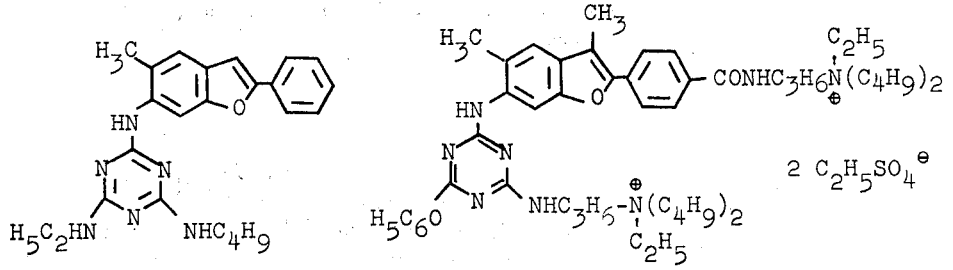

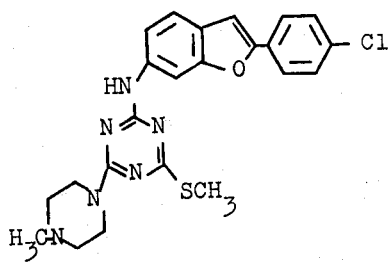

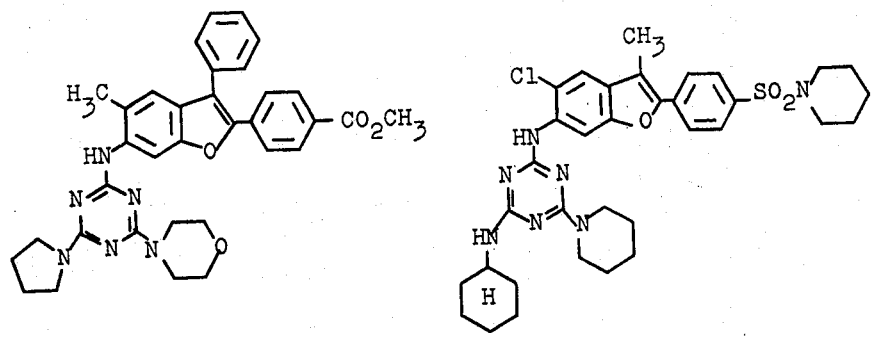

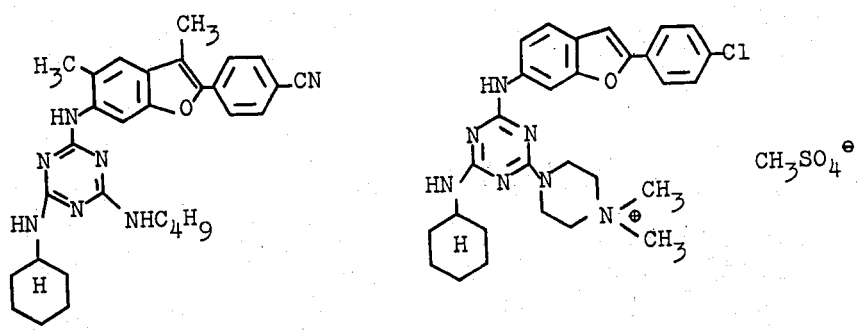

6-N-triazinylaminobenzofurans of formula (I) may be prepared by the reaction of a 6-aminobenzofuran of formula (II) with a chloro-1,3,5-triazine of formula (III) by a conventional method, for example according to Thurston, *J. Amer. Chem. Soc.* 73 (1951), 2982:

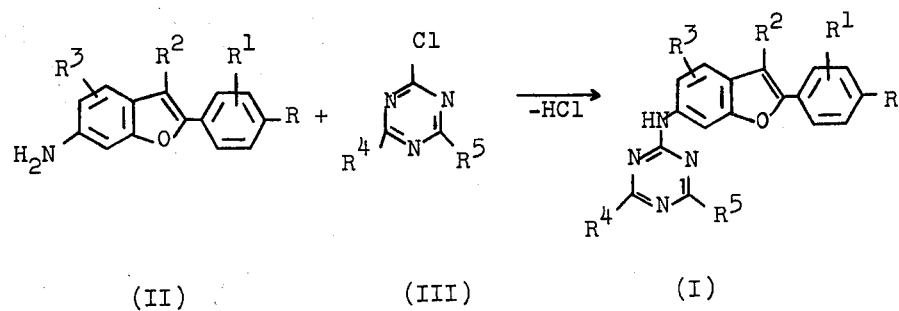

Compounds of the formula (II) may be prepared for example by the method disclosed in German Published Application (DOS) No. 2,304,265.

Another method of manufacture consists in reacting a compound of formula (IV) with a compound of the formula R⁴H and a compound of the formula R⁵H, preferably the corresponding alcoholates, thioalcoholates or amines in a suitable solvent in the presence of an acid acceptor at a temperature of from 0° to 150°C and preferably from 20° to 120°C:

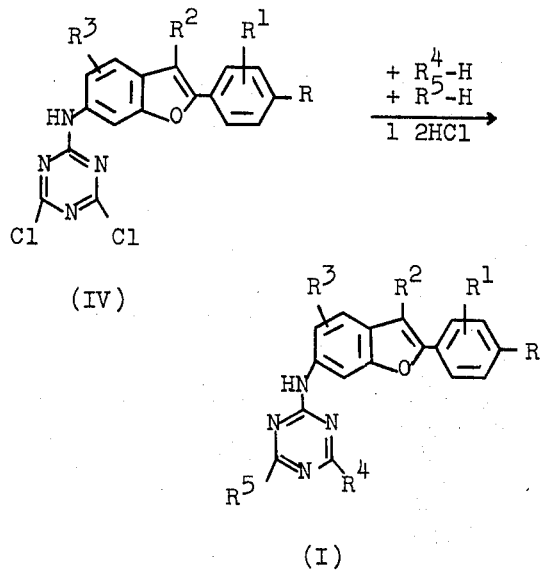

This process may also be carried out in two stages in which at first the compound of formula (V) is isolated:

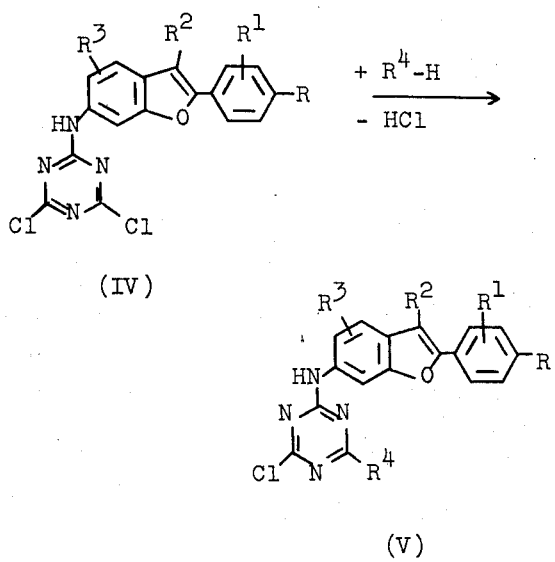

and this is then converted into a compound of formula (I) at a temperature of from 50° to 200°C and preferably at from 80° to 150°C. Reactions of this type are known per se (cf. Thurston, *J. Amer. Chem. Soc.* 73 (1951), 2982:

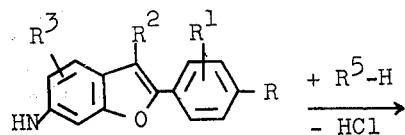

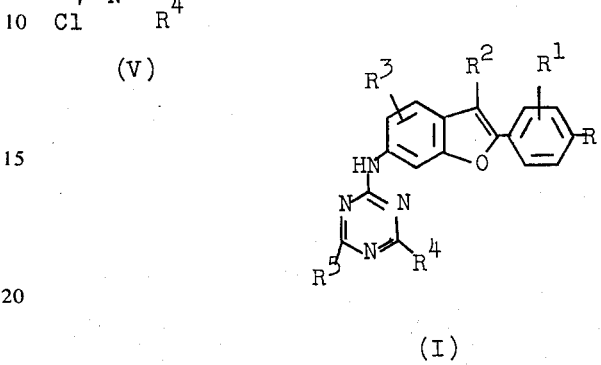

Examples of suitable solvents for the said reactions are water, methylformamide, dimethylformamide, N-methylpyrrolidone, acetone, methyl ethyl ketone, cyclohexanone, chlorobenzene, dioxane, methanol, ethanol, isopropanol, isobutanol, glycol monoethyl ether, ethylene glycol monomethyl ether and ethylene glycol monoethyl ether.

Examples of suitable compounds for use as acid acceptors in these reactions are NaOH, KOH, alkali metal carbonates such as $NaHCO_3$, $K_2CO_3$ and $Na_2CO_3$, alkali metal salts of lower fatty acids such as sodium formate and sodium acetate, the sodium and potassium salts of the alcohols being reacted or tertiary amines such as trimethylamine and triethylamine.

In the case when an amine is being reacted it may also be used in excess and thus be used as an acid acceptor.

The quaternization which may be carried out may be effected by alkylation by a conventional method, for example in one of the solvents already described.

The new compounds of formula (I) are colorless to pale yellowish substances which are suitable as optical brighteners for natural and synthetic fibers and particularly of polyamides, cellulose esters, polyesters and acrylonitrile polymers and also for the mass brightening of these substrates. The use and incorporation may take place by methods conventionally used for optical brighteners.

The new compounds and their manufacture are described in greater detail in the following Examples. The parts and percentages specified are by weight.

EXAMPLE 1

The optical brightener of the formula:

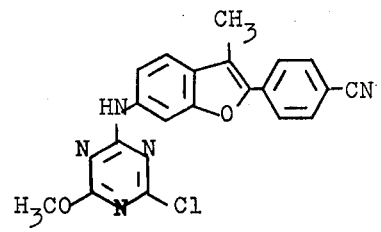

is obtained by suspending 5 parts of 6-amino-2-p-cyanophenyl-3-methylbenzofuran and 3.6 parts of 2,4-dichloro-6-methoxy-1,3,5-triazine in 50 parts of dimethylformamide, adding 6.7 parts of sodium bicarbonate and stirring the whole for five hours at ambient temperature. After the reaction mixture has been stirred into 300 parts of water the product is suction filtered and dried. The yield is 6.8 parts and the melting point is 290° to 293°C.

EXAMPLE 2

The optical brightener of the formula:

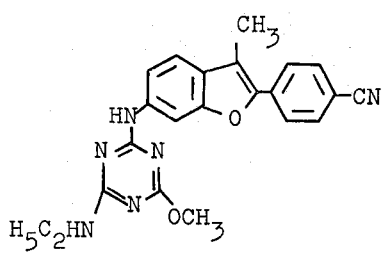

is obtained by dissolving 3.9 parts of the compound prepared in Example 1 in 200 parts of dimethylformamide, adding 0.5 part of ethylamine and 3.4 parts of sodium bicarbonate and stirring the whole for 1 hour at 140°C. After the whole has been cooled to ambient temperature it is stirred into 500 parts of water and the product is suction filtered and dried. The yield is 3.5 parts and the melting point is 127° to 128°C.

EXAMPLE 3

The optical brightener of the formula:

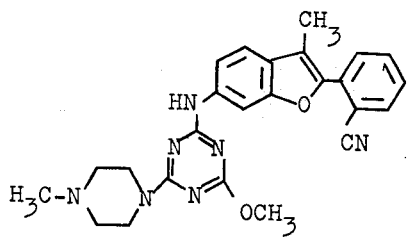

is obtained by repeating the procedure described in Example 2 but using 6-amino-2-o-cyanophenyl-3-methylbenzofuran instead of 6-amino-2-p-cyanophenyl-3-methylbenzofuran and 0.5 part of N-methylpiperazine instead of ethylamine. The yield is 2.2 parts and the melting point is 185° to 187°C.

EXAMPLE 4

The optical brightener of the formula:

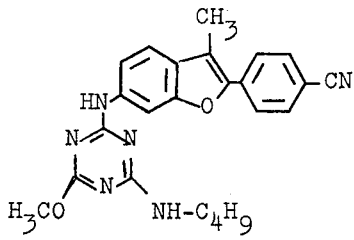

is obtained by repeating the procedure described in Example 2 but using 0.7 part of n-butylamine instead of ethylamined. The yield is 4.2 parts and the melting point is 205° to 207°C.

EXAMPLE 5

The optical brightener of the formula:

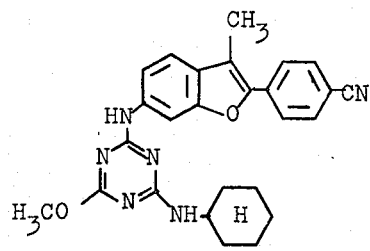

is obtained analogously to Example 2 by using 1 part of cyclohexylamine instead of ethylamine. The yield is 4.3 parts and the melting point is 260° to 262°C.

EXAMPLE 6

The optical brightener of the formula:

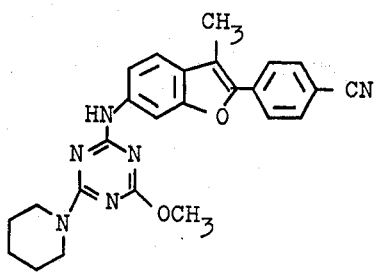

is obtained analogously to Example 2 by using 0.9 part of piperidine instead of ethylamine. The yield is 4 parts and the melting point is from 115° to 120°C.

EXAMPLE 7

The optical brightener of the formula:

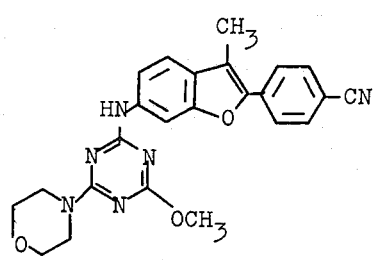

is obtained when an analogous procedure to that described in Example 2 is adopted but 0.9 part of morpholine is used instead of ethylamine. The yield is 4.2 parts and the melting point is 240° to 243°C. The yield is 4.2 parts and the melting point is 240° to 243°C.

EXAMPLE 8

The optical brightener of the formula:

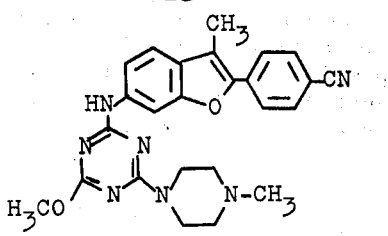

is obtained analogously to Example 2 by using 1 part of N-methylpiperazine instead of ethylamine. The yield is 4.2 parts and the melting point is 218° to 220°C.

EXAMPLE 9

The optical brightener of the formula:

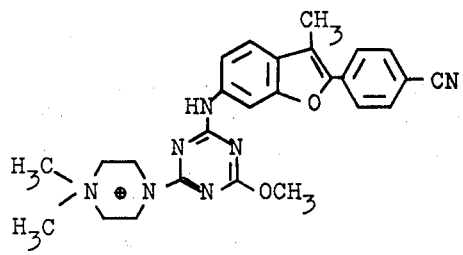

is obtained by dissolving 2.3 parts of the optical brightener from Example 8 in 100 parts of chlorobenzene, dripping in 0.8 part of dimethyl sulfate and stirring the whole for fifteen minutes at refluxing temperature. After cooling to 25°C the product is precipitated with 100 parts of petroleum ether 40–60, suction filtered and dried. The yield is 2.6 parts and the melting point is 268° to 270°C.

EXAMPLE 10

The optical brightener of the formula:

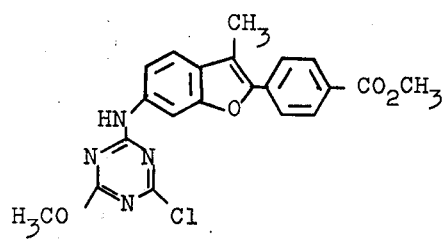

is obtained by repeating the procedure of Example 1 but using. 5.4 parts of 6-amino-2-p-carbomethoxyphenyl-3-methylbenzofuran instead of 6-amino-2-p-cyanophenyl-3-methylbenzofuran. The yield is 6.5 parts and the melting point is 240° to 242°C.

EXAMPLE 11

The optical brightener of the formula:

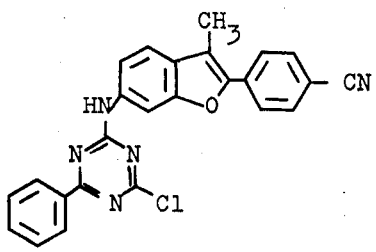

is obtained by suspending 5 parts of 6-amino-2-cyanophenyl-3-methylbenzofuran and 4.5 parts of 2,4-dichloro-6-phenyl-1,3,5-triazine in 200 parts of dimethylformamide, adding 6.7 parts of sodium bicarbonate and stirring the whole for three hours at room temperature. After 300 parts of water has been stirred in the product is suction filtered and dried. The yield is 7.2 parts and the melting point is 235°C.

EXAMPLE 12

The optical brightener of the formula:

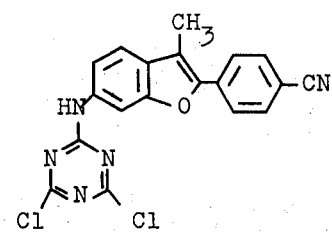

is obtained by dissolving 2.5 parts of 6-amino-2-p-cyanophenyl-3-methylbenzofuran and 1.8 parts of cyanuryl chloride in 100 parts of dioxane, adding 1.7 parts of sodium bicarbonate and stirring for one hour at ambient temperature. After stirring into 300 parts of water the product is suction filtered and dried. The yield is 2.6 parts and the melting point is 325° to 327°C.

EXAMPLE 13

The optical brightener of the formula:

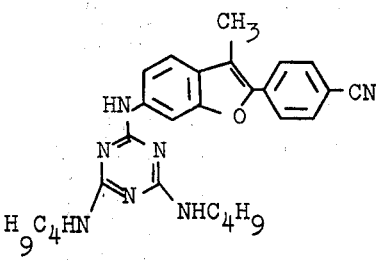

is obtained by dissolving 3.96 parts of the optical brightener from Example 12 in 200 parts of dimethylformamide, adding 1.4 parts of butylamine and 3.4 parts of sodium bicarbonate and stirring the whole for 30 minutes at 140°C. After cooling to 25°C it is stirred into 300 parts of water, suction filtered and dried. The yield is 4.1 parts and the melting point is 130° to 132°C.

EXAMPLE 14

The optical brightener of the formula:

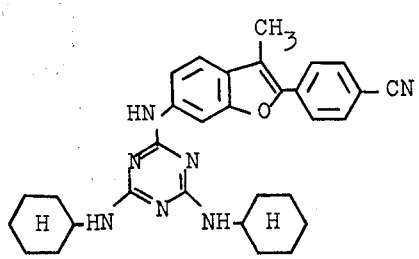

is obtained by adopting a procedure analogous to that in Example 13 but using 2 parts of cyclohexylamine instead of butylamine. The yield is 4.4 parts and the melting point is 245° to 247°C.

EXAMPLE 15

The optical brightener of the formula:

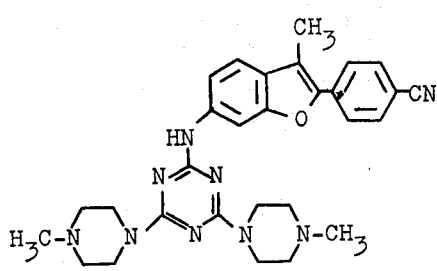

is obtained when a procedure analogous to that in Example 13 is followed but 2 parts of N-methylpiperazine is used instead of butylamine. The yield is 4 parts and the melting point is 150° to 152°C.

Compounds characterized in the following Table by their substituents are obtained analogously to the methods given above.

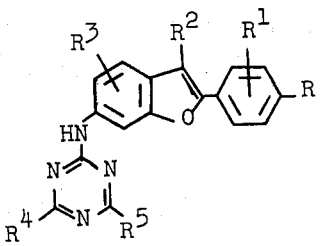

| Ex | R | R$^1$ | R$^2$ | R$^3$ |
|---|---|---|---|---|
| 16 | CN | H | CH$_3$ | H |
| 17 | H | H | " | H |
| 18 | Cl | H | " | H |
| 19 | Br | H | " | H |
| 20 | CO$_2$H | H | " | H |
| 21 | SO$_3$H | H | " | H |
| 22 | SO$_2$C$_6$H$_5$ | H | " | H |
| 23 | CH$_3$ | H | " | H |
| 24 | C$_2$H$_5$ | H | " | H |
| 25 | OCH$_3$ | H | " | H |
| 26 | OC$_2$H$_5$ | H | " | H |
| 27 | CO$_2$CH$_3$ | H | " | H |
| 28 | CO$_2$C$_4$H$_9$ | H | " | H |
| 29 | SO$_2$CH$_3$ | H | " | H |
| 30 | SO$_2$C$_2$H$_5$ | H | " | H |
| 31 | SO$_2$CH$_3$ | H | " | H |
| 32 | SO$_2$C$_4$H$_9$ | H | " | H |
| 33 | CONH$_2$ | H | " | H |
| 34 | SO$_2$NH$_2$ | H | " | H |
| 35 | CONHC$_4$H$_9$ | H | " | H |
| 36 | CONHC$_2$H$_5$ | H | " | H |
| 37 | CON(C$_4$H$_9$)$_2$ | H | " | H |
| 38 | CON(CH$_3$)$_2$ | H | " | H |
| 39 | SO$_2$NHC$_4$H$_9$ | H | " | H |
| 40 | SO$_2$NHCH$_3$ | H | " | H |
| 41 | SO$_2$N(C$_4$H$_9$)$_2$ | H | " | H |
| 42 | SO$_2$N(CH$_3$)$_2$ | H | " | H |
| 43 | CONHC$_2$H$_4$OH | H | " | H |
| 44 | SO$_2$NHC$_2$H$_4$OH | H | " | H |
| 45 | CONHCN(CH$_3$)CH$_2$OH | H | " | H |
| 46 | SO$_2$NHCH(CH$_3$)CH$_2$OH | H | " | H |
| 47 | CONH-cyclohexyl | H | " | H |
| 48 | SO$_2$NHCH$_2$-phenyl | H | " | H |
| 49 | SO$_2$NH-phenyl | H | " | H |
| 50 | CON-morpholino | H | " | H |
| 51 | CON-pyrrolidino | H | " | H |
| 52 | SO$_2$N-morpholino | H | " | H |
| 53 | SO$_2$N-pyrrolidino | H | " | H |

-continued

| No. | | | | |
|---|---|---|---|---|
| 54 | CON⌬NH (piperazine) | H | ″ | H |
| 55 | SO₂N⌬ (piperidine) | H | ″ | H |
| 56 | CON⌬N—CH₃ | H | ″ | H |
| 57 | SO₂N⌬NH | H | ″ | H |
| 58 | CON⌬ (piperidine) | H | ″ | H |
| 59 | SO₂N⌬N—CH₃ | H | ″ | H |
| 60 | CON⌬N—C₂H₄OH | H | ″ | H |
| 61 | H | CN | ″ | H |
| 62 | H | CO₂H | ″ | H |
| 63 | H | CO₂C₄H₉ | ″ | H |
| 64 | H | SO₂C₆H₅ | ″ | H |
| 65 | H | CONHC₄H₉ | ″ | H |
| 66 | H | CON(C₂H₅)₂ | ″ | H |
| 67 | H | CONHC₂H₄OH | ″ | H |
| 68 | H | CONH—C₆H₁₁ (cyclohexyl) | ″ | H |
| 69 | H | CON⌬N—CH₃ | ″ | H |
| 70 | H | CON⌬ (piperidine) | ″ | H |
| 71 | H | SO₂N⌬O (morpholine) | ″ | H |
| 72 | H | CON⌬N—C₂H₄OH | ″ | H |
| 73 | H | CN | H | H |
| 74 | H | CN | C₂H₅ | H |
| 75 | H | CN | C₆H₅ | H |
| 76 | CN | H | CH₃ | Cl |
| 77 | ″ | H | ″ | Br |
| 78 | ″ | H | ″ | CO₂H |
| 79 | ″ | H | ″ | SO₃H |
| 80 | ″ | H | ″ | SO₂C₆H₅ |
| 81 | ″ | H | ″ | CH₃ |
| 82 | ″ | H | ″ | C₂H₅ |
| 83 | ″ | H | ″ | OCH₃ |
| 84 | ″ | H | ″ | OC₂H₅ |
| 85 | ″ | H | ″ | CO₂CH₃ |
| 86 | ″ | H | ″ | CO₂C₃H₇ |
| 87 | CN | H | ″ | SO₂CH₃ |
| 88 | ″ | H | ″ | SO₂C₂H₅ |
| 89 | ″ | H | ″ | SO₃C₄H₉ |
| 90 | ″ | H | ″ | CONH₂ |
| 91 | ″ | H | ″ | CONHC₄H₉ |
| 92 | ″ | H | ″ | SO₂N(CH₃)₂ |
| 93 | ″ | H | ″ | CONH—C₆H₁₁ |

| | | | | |
|---|---|---|---|---|
| 94 | '' | H | '' | CON−morpholine |
| 95 | '' | H | '' | SO₂−N(piperazine)N−CH₃ |
| 96 | '' | H | '' | CON−pyrrolidine |
| 97 | '' | H | '' | SO₂N(piperazine)NH |
| 98 | '' | H | '' | |
| 99 | CN | H | '' | H |
| 100 | '' | H | '' | H |
| 101 | '' | H | '' | H |
| 102 | '' | H | '' | H |
| 103 | '' | H | '' | H |
| 104 | '' | H | '' | H |
| 105 | '' | H | '' | H |
| 106 | '' | H | '' | H |
| 107 | '' | H | '' | H |
| 108 | CN | H | CH₃ | H |
| 109 | '' | H | '' | H |
| 110 | '' | H | '' | H |
| 111 | '' | H | '' | H |
| 112 | '' | H | '' | H |
| 113 | '' | H | '' | H |
| 114 | '' | H | '' | H |
| 115 | '' | H | '' | H |
| 116 | '' | H | '' | H |
| 117 | '' | H | '' | H |
| 118 | '' | H | '' | H |
| 119 | '' | H | '' | H |
| 120 | '' | H | '' | H |
| 121 | '' | H | '' | H |
| 122 | '' | H | '' | H |
| 123 | '' | H | '' | H |
| 124 | '' | H | '' | H |
| 125 | '' | H | '' | H |
| 126 | '' | H | '' | H |
| 127 | '' | H | '' | H |
| 128 | '' | H | '' | H |
| 129 | '' | H | '' | H |
| 130 | '' | H | '' | H |
| 131 | CN | H | CH₃ | H |
| 132 | '' | H | '' | H |
| 133 | '' | H | '' | H |
| 134 | '' | H | '' | H |
| 135 | '' | H | '' | H |
| 136 | '' | H | '' | H |
| 137 | '' | H | '' | H |
| 138 | '' | H | '' | H |
| 139 | '' | H | '' | H |
| 140 | '' | H | '' | H |
| 141 | '' | H | '' | H |
| 142 | '' | H | '' | H |
| 143 | '' | H | '' | H |
| 144 | '' | H | '' | H |
| 145 | '' | H | '' | H |
| 146 | '' | H | '' | H |
| 147 | '' | H | '' | H |
| 148 | '' | H | '' | H |
| 149 | '' | H | '' | H |
| 150 | '' | H | '' | H |
| 151 | '' | H | '' | H |
| 152 | '' | H | '' | H |
| 153 | CN | H | CH₃ | H |
| 154 | '' | H | '' | H |
| 155 | '' | H | '' | H |
| 156 | '' | H | '' | H |
| 157 | '' | H | '' | H |
| 158 | '' | H | '' | H |
| 159 | '' | H | '' | H |
| 160 | '' | H | '' | H |
| 161 | '' | H | '' | H |
| 162 | '' | H | '' | H |
| 163 | '' | H | '' | H |
| 164 | '' | H | '' | H |
| 165 | '' | H | '' | H |
| 166 | '' | H | '' | H |
| 167 | '' | H | '' | H |
| 168 | '' | H | '' | H |
| 169 | '' | H | '' | H |
| 170 | '' | H | '' | H |
| 171 | '' | H | '' | H |
| 172 | '' | H | '' | H |

-continued

|  |  |  |  |  |
|---|---|---|---|---|
| 173 | '' | H | '' | H |
| 174 | '' | H | '' | H |
| 175 | '' | H | '' | H |
| 176 | '' | H | '' | H |
| 177 | CN | H | $CH_3$ | H |
| 178 | '' | H | '' | H |
| 179 | '' | H | '' | H |
| 180 | '' | H | '' | H |
| 181 | '' | H | '' | H |
| 182 | '' | H | '' | H |
| 183 | '' | H | '' | H |
| 184 | '' | H | '' | H |
| 185 | '' | H | '' | H |
| 186 | '' | H | '' | H |
| 187 | '' | H | '' | H |
| 188 | '' | H | '' | H |
| 189 | '' | H | '' | H |
| 190 | '' | H | '' | H |
| 191 | '' | H | '' | H |
| 192 | '' | H | '' | H |
| 193 | '' | H | '' | H |
| 194 | '' | H | '' | H |
| 195 | '' | H | '' | H |
| 196 | '' | H | '' | H |
| 197 | '' | H | '' | H |
| 198 | CN | H | '' | H |
| 199 | '' | H | '' | H |
| 200 | '' | H | '' | H |
| 201 | '' | H | '' | H |
| 202 | '' | H | '' | H |
| 203 | CON | H | $CH_3$ | H |
| 204 | H | CN | $C_2H_5$ | H |
| 205 | H | H | H | H |
| 206 | $CO_2C_2H_5$ | H | $CH_3$ | H |
| 207 | H | $CO_2CH_3$ | $C_2H_5$ | H |
| 208 | $SO_2NH_2$ | H | $CH_3$ | H |
| 209 | H | CN | $CH_3$ | H |
| 210 | $CONC_4H_9$ | Cl | H | H |
| 211 | $CO_2C_2H_4OC_2H_5$ | H | $CH_3$ | H |
| 212 | $CO_2C_2H_4OCH_3$ | H | $CH_3$ | $CH_3$ |
| 213 | $SO_2N\ O$ | H | $CH_3$ | H |
| 214 | H | H | H | $CH_3$ |
| 215 | $CONHC_3H_6N(C_4H_9)_2$ | H | $CH_2$ | $CH_3$ |
| 216 | Cl | H | H | H |
| 217 | $CO_2CH_3$ | H | $C_6H_5$ | $CH_3$ |
| 218 | $SO_2N$ | H | $CH_3$ | Cl |
| 219 | CN | H | $CH_3$ | $CH_3$ |
| 220 | Cl | H | H | H |

| Ex. | $R^4$ | $R^5$ |
|---|---|---|
| 16 | $OCH_3$ | $OCH_3$ |
| 17 | '' | '' |
| 18 | '' | '' |
| 19 | '' | '' |
| 20 | '' | '' |
| 21 | '' | '' |
| 22 | '' | '' |
| 23 | '' | '' |
| 24 | '' | '' |
| 25 | '' | '' |
| 26 | '' | '' |
| 27 | '' | '' |
| 28 | '' | '' |
| 29 | '' | '' |
| 30 | '' | '' |
| 31 | '' | '' |
| 32 | '' | '' |
| 33 | '' | '' |
| 34 | '' | '' |
| 35 | '' | '' |
| 36 | '' | '' |
| 37 | '' | '' |
| 38 | '' | '' |
| 39 | '' | '' |
| 40 | '' | '' |
| 41 | '' | '' |
| 42 | '' | '' |
| 43 | '' | '' |
| 44 | '' | '' |
| 45 | '' | '' |
| 46 | '' | '' |
| 47 | '' | '' |
| 48 | '' | '' |
| 49 | '' | '' |
| 50 | '' | '' |
| 51 | '' | '' |
| 52 | '' | '' |
| 53 | '' | '' |
| 54 | '' | '' |
| 55 | '' | '' |
| 56 | '' | '' |
| 57 | '' | '' |

| | | |
|---|---|---|
| 58 | '' | '' |
| 59 | '' | '' |
| 60 | '' | '' |
| 61 | '' | '' |
| 62 | '' | '' |
| 63 | '' | '' |
| 64 | '' | '' |
| 65 | '' | '' |
| 66 | '' | '' |
| 67 | '' | '' |
| 68 | '' | '' |
| 69 | '' | '' |
| 70 | '' | '' |
| 71 | '' | '' |
| 72 | '' | '' |
| 73 | '' | '' |
| 74 | '' | '' |
| 75 | '' | '' |
| 76 | '' | '' |
| 77 | '' | '' |
| 78 | '' | '' |
| 79 | '' | '' |
| 80 | '' | '' |
| 81 | '' | '' |
| 82 | '' | '' |
| 83 | '' | '' |
| 84 | '' | '' |
| 85 | '' | '' |
| 86 | '' | '' |
| 87 | '' | '' |
| 88 | '' | '' |
| 89 | '' | '' |
| 90 | '' | '' |
| 91 | '' | '' |
| 92 | '' | '' |
| 93 | '' | '' |
| 94 | '' | '' |
| 95 | '' | '' |
| 96 | '' | '' |
| 97 | '' | '' |
| 98 | H | '' |
| 99 | $CH_3$ | '' |
| 100 | $C_4H_9$ | '' |
| 101 | cyclohexyl-H | '' |
| 102 | $-CH_2-$phenyl | '' |
| 103 | $C_2H_4-$phenyl | '' |
| 104 | $C_3H_6-$phenyl | '' |
| 105 | phenyl | '' |
| 106 | Cl | '' |
| 107 | Br | '' |
| 108 | OH | '' |
| 109 | $OC_2H_5$ | '' |
| 110 | $OC_3H_7$ | '' |
| 111 | $OC_4H_9$ | '' |
| 112 | $-O-$phenyl | '' |
| 113 | $-S-CH_3$ | '' |
| 114 | $-S-C_2H_5$ | '' |
| 115 | $-S-$phenyl | '' |
| 116 | $-NH-(CH_2)_3-NH_2$ | '' |
| 117 | $-NH-(CH_2)_3-NHCH_3$ | '' |
| 118 | $-NH(CH_2)_3-NHC_4H_9$ | '' |

| | | |
|---|---|---|
| 119 | —NH(CH$_2$)$_3$—N(C$_8$H$_{17}$)$_2$ | " |
| 120 | NH(CH$_2$)$_3$—NHC$_2$H$_4$OH | " |
| 121 | NH(CH$_2$)$_3$—NHC$_2$H$_4$OCH$_3$ | " |
| 122 | NH(CH$_2$)$_3$—N(C$_2$H$_4$OC$_2$H$_5$)$_2$ | " |
| 123 | NHC$_2$H$_4$NH$_2$ | " |
| 124 | NHC$_6$H$_{12}$—NH$_2$ | " |
| 125 | 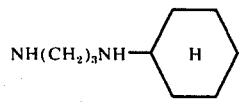 | " |
| 126 | | " |
| 127 | | " |
| 128 | | " |
| 129 | | " |
| 130 | | " |
| 131 | | " |
| 132 | | " |
| 133 | | " |
| 134 | NH$_2$ | " |
| 135 | NHC$_2$H$_5$ | " |
| 136 | NHC$_8$H$_{17}$ | " |
| 137 | N(C$_4$H$_9$)$_2$ | " |
| 138 | NHC$_2$H$_4$OH | " |
| 139 | NHC$_2$H$_4$OC$_2$H$_5$ | " |
| 140 | NHC$_2$H$_4$NH$_2$ | " |
| 141 | NHC$_6$H$_{12}$NH$_2$ | " |
| 142 | 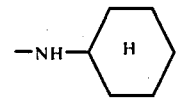 | " |
| 143 | | " |
| 144 | | " |
| 145 | | " |
| 146 | | " |
| 147 | | " |

-continued

| | | |
|---|---|---|
| 148 | —N(piperazine)N—CH₃ | " |
| 149 | —N(piperidine) | " |
| 150 | —N(piperazine)N—C₂H₄OH | " |
| 151 | OC₂H₅ | H |
| 152 | " | CH₃ |
| 153 | OC₂H₅ | C₄H₉ |
| 154 | " | cyclohexyl-H |
| 155 | " | —CH₂—C₆H₅ |
| 156 | " | —C₂H₄—C₆H₅ |
| 157 | " | —C₂H₆—C₆H₅ |
| 158 | " | —C₆H₅ (phenyl) |
| 159 | " | Cl |
| 160 | " | Br |
| 161 | " | OH |
| 162 | " | OCH₃ |
| 163 | " | OC₃H₇ |
| 164 | " | OC₄H₉ |
| 165 | " | OC₆H₅ |
| 166 | " | S—CH₃ |
| 167 | " | S—C₂H₅ |
| 168 | " | —S—C₆H₅ |
| 169 | " | —NH—(CH₂)₃NH₂ |
| 170 | " | —NH—(CH₂)₃NHCH₃ |
| 171 | " | —NH(CH₂)₃NHC₄H₉ |
| 172 | " | —NH(CH₂)₃—N(C₈H₁₇)₂ |
| 173 | " | —NH(CH₂)₃NHC₂H₄OH |
| 174 | " | —NH(CH₂)₃—NHC₂H₄OH |
| 175 | " | NH(CH₂)₃—N(C₂H₄OC₂H₅)₂ |
| 176 | " | NHC₂H₄NH₂ |
| 177 | " | NHC₆H₁₂—NH₂ |
| 178 | " | NH(CH₂)₃NH—cyclohexyl-H |
| 179 | " | NH(CH₂)₃NHCH₂—C₆H₅ |
| 180 | " | NH(CH₂)₃—NH—C₆H₅ |
| 181 | " | NH(CH₂)₃—N(piperazine)NH |

-continued
| | | |
|---|---|---|
| 182 | " | 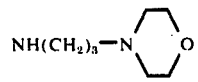 |
| 183 | " | 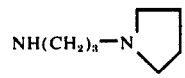 |
| 184 | " | 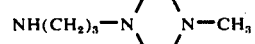 |
| 185 | " | 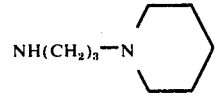 |
| 186 | " | 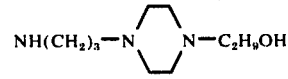 |
| 187 | " | $NH_2$ |
| 188 | " | $NHC_2H_5$ |
| 189 | " | $NHC_8H_{17}$ |
| 190 | " | $N(C_4H_9)_2$ |
| 191 | " | $NHC_2H_4OH$ |
| 192 | " | $NHC_2H_4OC_2H_5$ |
| 193 | " | $NHC_2H_4NH_2$ |
| 194 | " | $NHC_6H_{12}NH_2$ |
| 195 | " | 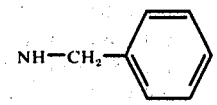 |
| 196 | " | 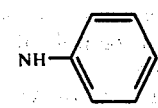 |
| 197 | " |  |
| 198 | " |  |
| 199 | " |  |
| 200 | " | 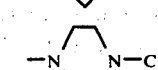 |
| 201 | " | 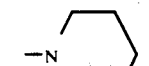 |
| 202 | " | 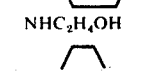 |
| 203 | N | $NHC_2H_4OH$ |
| 204 | $OC_4H_9$ | 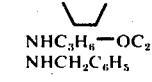 |
| 205 | N N—$CH_3$ | $NHC_3H_6$—$OC_2H_5$ |
| 206 | Cl | $NHCH_2C_6H_5$ |
| 207 | $OCH_3$ | 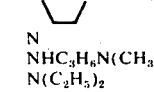 |
| 208 | N | N |
| 209 | $OC_2H_5$ | $NHC_3H_6N(CH_3)_2$ |
| 210 | $N(C_2H_5)_2$ | $N(C_2H_5)_2$ |
| 211 | $NH_2$ | 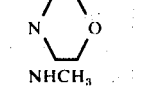 |
| 212 | $NHCH_3$ | $NHCH_3$ |

-continued

| 213 | OH | | |
| --- | --- | --- | --- |
| 214 | NHC$_2$H$_5$ | 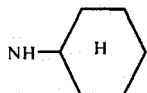 | |
| 215 | OC$_6$H$_5$ | NHC$_4$H$_9$ | |
| 216 | SCH$_3$ | NHC$_3$H$_6$N(C$_4$H$_9$)$_2$ | |
| 217 |  | 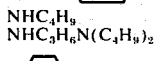 | |
| 218 | N | 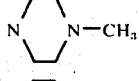 | |
| 219 | NHC$_4$H$_9$ | 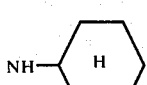 | |
| 220 | 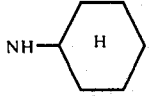 | 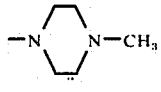 | |

We claim:
1. A 6-N-triazinylamino-benzofuran of the formula

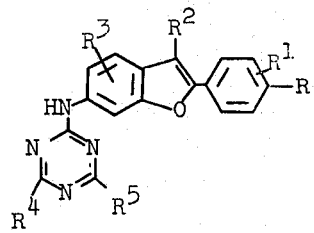

wherein:
R, R$^1$ and R$^3$ are independently of one another hydrogen, chlorine, bromine, cyano, carboxyl, hydroxysulfonyl, phenylsulfony, methyl, ethyl, methoxy, ethoxy, alkoxycarbonyl or alkoxyethoxycarbonyl of 1 to 4 carbon atoms in the alkoxy, methylsulfonyl, ethylsulfonyl, alkoxysulfonyl of 1 to 4 carbon atoms in the alkoxy, carbamoyl or sulfamoyl substituted on nitrogen once or twice by alkyl of 1 to 4 carbon atoms, hydroxyalkyl of 2 or 3 carbon atoms, cyclohexyl, benzyl, phenylethyl or phenyl; carbo-pyrrolidide, carbo-piperidide, carbo-piperazide, carbo-N-methyl-piperazide, carbo-N-β-hydroxyethylpiperazide, sulfo-pyrrolidide, sulfopiperidide, sulfo-piperazide, sulfo-N-methyl-piperazide or sulfo-N-β-hydroxyethylpiperazide;

R$^2$ is hydrogen, methyl, ethyl or phenyl;
R$^4$ and R$^5$ are independently of one another hydrogen, alkyl of 1 to 4 carbon atoms, cyclohexyl, benzyl, phenylethyl, phenylpropyl, phenyl, chlorine, bromine, hydroxy, alkoxy of 1 to 8 carbon atoms, phenoxy, methylmercapto, ethylmercapto, phenylmercapto,

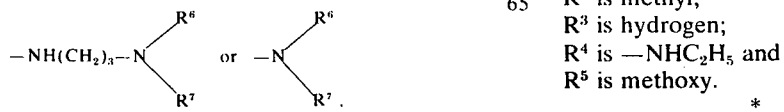

R$^6$ and R$^7$ are independently of one another hydrogen, alkyl of 1 to 8 carbon atoms, hydroxyalkyl of 2 to 8 carbon atoms, alkoxyalkyl of 1 to 4 carbon atoms in the alkoxy and 2 or 3 carbon atoms in the alkyl, aminoethyl, aminohexyl, cyclohexyl, norbornyl, benzyl, phenylethyl, phenylpropyl or phenyl and R$^6$ and R$^7$ together with the nitrogen are pyrrolidino, piperidino, piperazino, N-methyl-piperazino or N-β-hydroxyethylpiperazino.

2. A benzofuran according to the formula in claim 1, wherein R$^2$ and R$^3$ are hydrogen or methyl.

3. A benzofuran according to the formula in claim 1, wherein
R is hydrogen or cyano
R$^1$ is hydrogen, chlorine or cyano,
R$^2$ is hydrogen or methyl,
R$^3$ is hydrogen and
R$^4$ and R$^5$ are independently of one another methoxy,

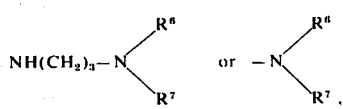

R$^6$ and R$^7$ having the meanings given in claim 1.

4. A benzofuran according to claim 3, wherein
R$^6$ and R$^7$ are alkyl of 1 to 4 carbon atoms and
R$^6$ and R$^7$ together with the nitrogen are pyrrolidino, piperidino, piperazino or N-methyl-piperazino.

5. A benzofuran according to the formula of claim 1 wherein:
R is hydrogen;
R$^1$ is cyano;
R$^2$ is methyl;
R$^3$ is hydrogen;
R$^4$ is —NHC$_2$H$_5$ and
R$^5$ is methoxy.

* * * * *